(12) United States Patent
Wallace

(10) Patent No.: US 10,959,750 B2
(45) Date of Patent: Mar. 30, 2021

(54) METHODS AND DEVICES FOR REMOVING OBSTRUCTING MATERIAL FROM THE HUMAN BODY

(71) Applicant: CARDIOPROLIFIC INC., Reno, NV (US)

(72) Inventor: Michael P. Wallace, Pleasanton, CA (US)

(73) Assignee: CARDIOPROLIFIC INC., Reno, NV (US)

( * ) Notice: Subject to any disclaimer, the term of this patent is extended or adjusted under 35 U.S.C. 154(b) by 220 days.

(21) Appl. No.: 15/225,123

(22) Filed: Aug. 1, 2016

(65) Prior Publication Data

US 2017/0027604 A1    Feb. 2, 2017

Related U.S. Application Data

(63) Continuation of application No. 14/212,987, filed on Mar. 14, 2014, now abandoned, which is a continuation-in-part of application No. 13/870,777, filed on Apr. 25, 2013, now abandoned.

(51) Int. Cl.
| | |
|---|---|
| *A61B 17/3207* | (2006.01) |
| *A61M 25/01* | (2006.01) |
| *A61M 3/02* | (2006.01) |
| *A61B 17/22* | (2006.01) |

(Continued)

(52) U.S. Cl.
CPC ...... *A61B 17/320758* (2013.01); *A61B 17/22* (2013.01); *A61F 7/0085* (2013.01); *A61M 3/0283* (2013.01); *A61M 25/0108* (2013.01); *A61B 2017/00734* (2013.01); *A61B 2017/00778* (2013.01); *A61B 2017/00893* (2013.01); *A61B 2017/22038* (2013.01); *A61B 2017/22079* (2013.01); *A61B 2017/320733* (2013.01); *A61B 2017/320766* (2013.01); *A61B 2017/320775* (2013.01); *A61B 2217/005* (2013.01); *A61B 2217/007* (2013.01);
(Continued)

(58) Field of Classification Search
CPC ........ A61B 17/320758; A61B 17/3207; A61B 17/320725; A61B 2017/320766; A61B 2017/320775; A61B 2017/320791; A61B 2017/320732; A61B 2017/320783; A61B 17/1631; A61B 17/32075; A61B 17/320783; A61B 2017/320741; A61B 2017/320733; A61B 17/22; Y10T 74/18024; Y10T 74/18032; Y10T 74/1804; Y10T 74/18048; Y10T 74/18056; Y10T 74/18336; F01B 3/02
See application file for complete search history.

(56) References Cited

U.S. PATENT DOCUMENTS

| | | | |
|---|---|---|---|
| 4,737,153 | A | 4/1988 | Shimamura |
| 4,966,604 | A | 10/1990 | Reiss |
| 5,047,040 | A | 9/1991 | Simpson |

(Continued)

*Primary Examiner* — Tuan V Nguyen

(57) ABSTRACT

A device for removing obstructive material from a patient may include an elongate rotational member having a distal end and a proximal end, an internal irrigation catheter at least partially surrounding the rotational member, and an aspiration catheter at least partially surrounding the rotational member and the irrigation catheter. The distal portion of the rotational member is configured to change compliance of the obstructive material and facilitate obstructive material aspiration outside the patient.

21 Claims, 10 Drawing Sheets

(51) Int. Cl.
*A61F 7/00* (2006.01)
*A61B 17/00* (2006.01)

(52) U.S. Cl.
CPC .............. *A61M 2202/0014* (2013.01); *A61M 2202/0413* (2013.01); *A61M 2202/06* (2013.01); *Y10T 74/18024* (2015.01)

(56) References Cited

U.S. PATENT DOCUMENTS

| | | | |
|---|---|---|---|
| 5,180,376 A | 7/1993 | Evans | |
| 5,226,909 A * | 7/1993 | Evans | A61B 17/320783 604/22 |
| 5,366,464 A * | 11/1994 | Belknap | A61B 17/320758 606/159 |
| 5,376,100 A | 12/1994 | Lefebvre | |
| 5,462,529 A | 10/1995 | Simpson | |
| 5,501,694 A | 10/1996 | Ressemann | |
| 5,569,275 A | 10/1996 | Kotula | |
| 5,630,806 A | 5/1997 | Inagaki | |
| 5,676,497 A * | 10/1997 | Kim | B23D 61/003 144/35.2 |
| 5,766,191 A | 6/1998 | Treotola | |
| 5,843,031 A | 12/1998 | Hermann | |
| 5,843,103 A * | 12/1998 | Wulfman | A61B 17/320758 606/159 |
| 5,873,882 A | 2/1999 | Straub | |
| 5,911,734 A | 6/1999 | Tsugita | |
| 5,947,940 A | 9/1999 | Beisel | |
| 5,972,019 A | 10/1999 | Engelson | |
| 6,193,735 B1 * | 2/2001 | Stevens | A61B 17/320758 600/585 |
| 6,402,745 B1 * | 6/2002 | Wilk | A61B 18/1492 606/157 |
| 7,037,316 B2 | 5/2006 | McGuckin | |
| 7,179,269 B2 | 2/2007 | Welch | |
| 7,235,088 B2 | 6/2007 | Pintor | |
| 7,666,161 B2 | 2/2010 | Nash | |
| 7,763,010 B2 | 7/2010 | Evans | |
| 7,842,006 B2 | 11/2010 | Wang | |
| 7,842,055 B2 | 11/2010 | Pintor | |
| 7,938,820 B2 | 5/2011 | Webster | |
| 7,942,852 B2 | 5/2011 | Mas | |
| 8,062,317 B2 | 11/2011 | McGukin | |
| 8,366,620 B2 | 2/2013 | Nita | |
| 8,414,543 B2 | 4/2013 | McGukin | |
| 8,535,290 B2 | 9/2013 | Evans | |
| 8,545,447 B2 | 10/2013 | Demarais | |
| 9,339,288 B2 * | 5/2016 | Sullivan | A61B 17/32002 |
| 9,539,019 B2 * | 1/2017 | Sullivan | A61B 17/32002 |
| 10,130,389 B2 * | 11/2018 | Sullivan | A61B 17/32002 |
| 2004/0215222 A1 * | 10/2004 | krivoruchko | A61B 17/320725 606/159 |
| 2009/0270812 A1 * | 10/2009 | Litscher | A61B 1/303 604/164.01 |
| 2009/0270896 A1 * | 10/2009 | Sullivan | A61B 17/32002 606/170 |
| 2010/0023035 A1 * | 1/2010 | Kontos | A61B 17/320725 606/159 |
| 2011/0077674 A1 * | 3/2011 | Sullivan | A61B 17/32002 606/170 |
| 2011/0160621 A1 | 6/2011 | Nita | |
| 2011/0313328 A1 | 12/2011 | Nita | |
| 2011/0319927 A1 | 12/2011 | Nita | |
| 2012/0078140 A1 | 3/2012 | Nita | |
| 2012/0116429 A1 * | 5/2012 | Levine | A61B 17/320758 606/159 |
| 2012/0179073 A1 | 7/2012 | Nita | |
| 2012/0330196 A1 | 12/2012 | Nita | |
| 2013/0158578 A1 | 6/2013 | Ghodke | |
| 2013/0325003 A1 * | 12/2013 | Kapur | A61B 18/1492 606/46 |
| 2014/0056842 A1 | 2/2014 | Sackner-Berstein | |
| 2014/0316450 A1 * | 10/2014 | Higgins | A61B 17/320758 606/159 |

\* cited by examiner

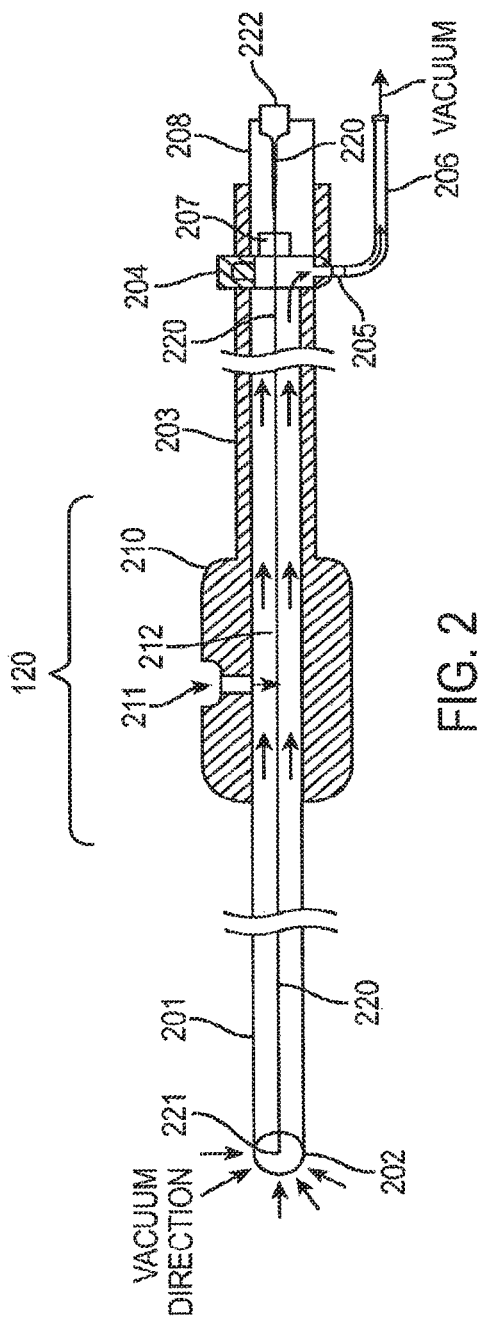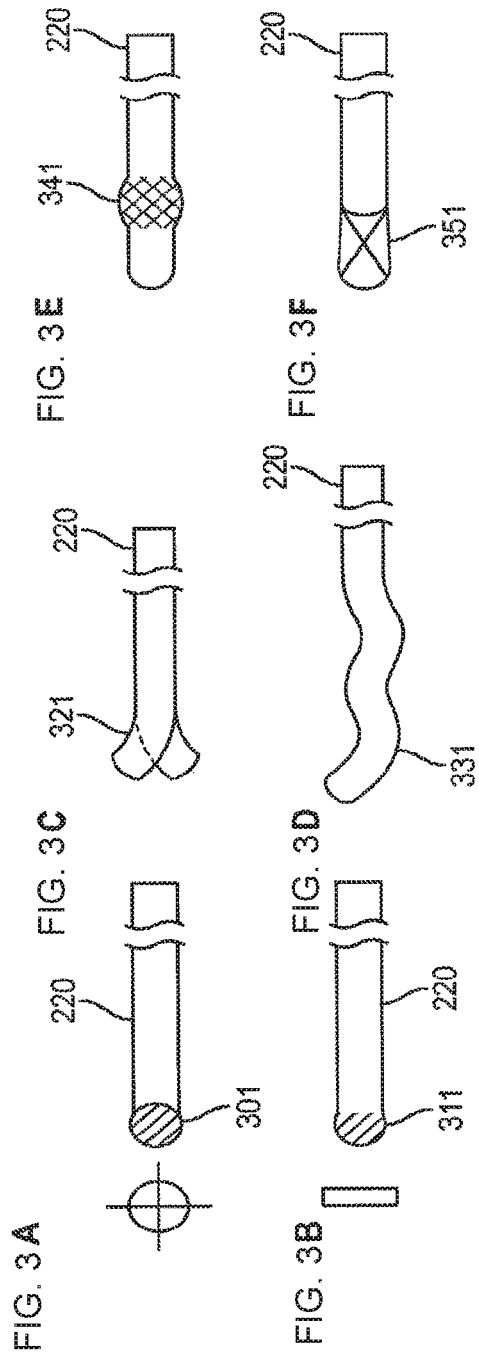

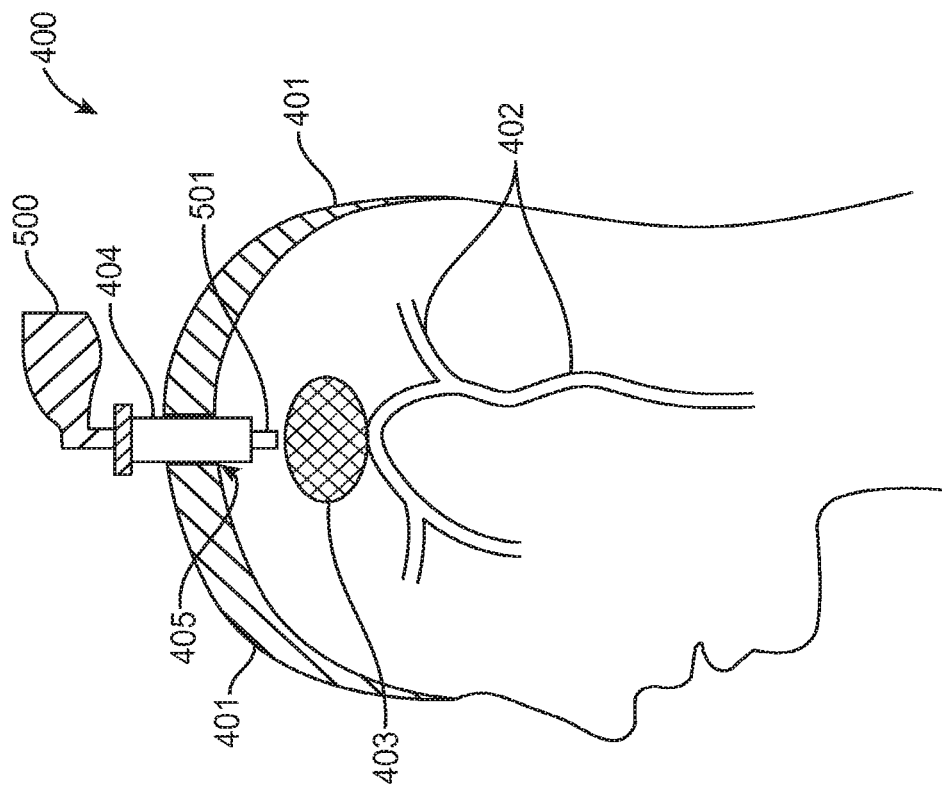
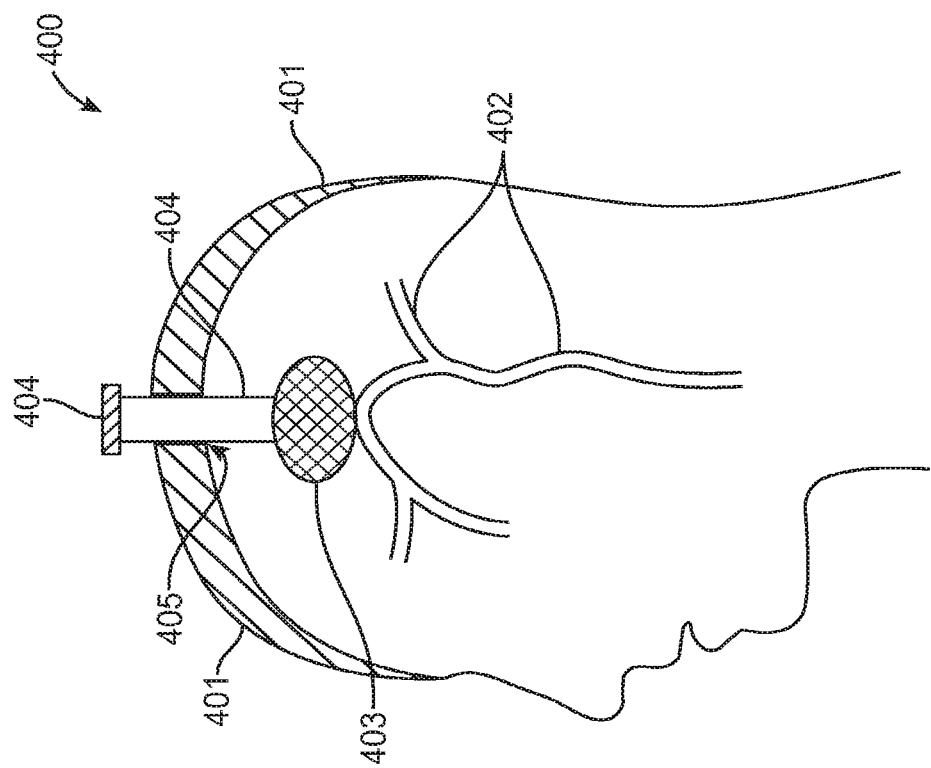
FIG. 4A
FIG. 4B

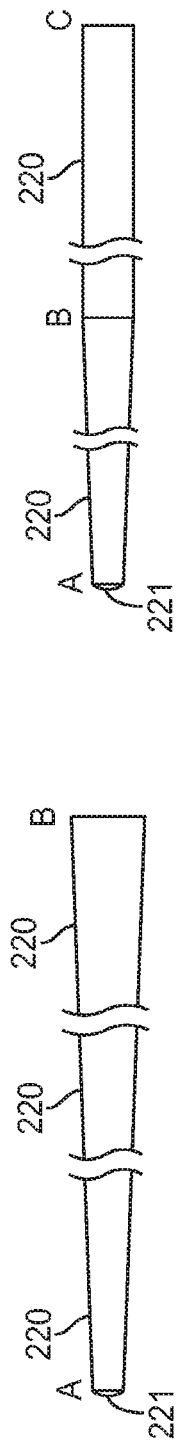
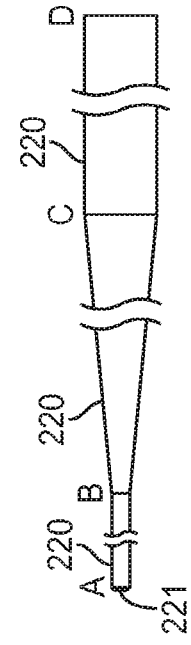
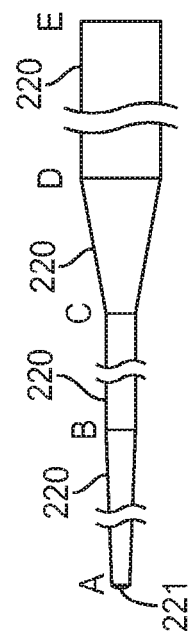
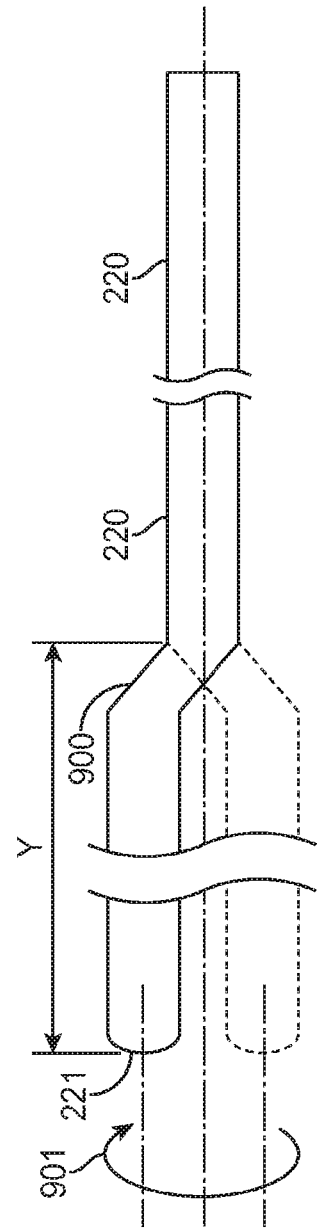

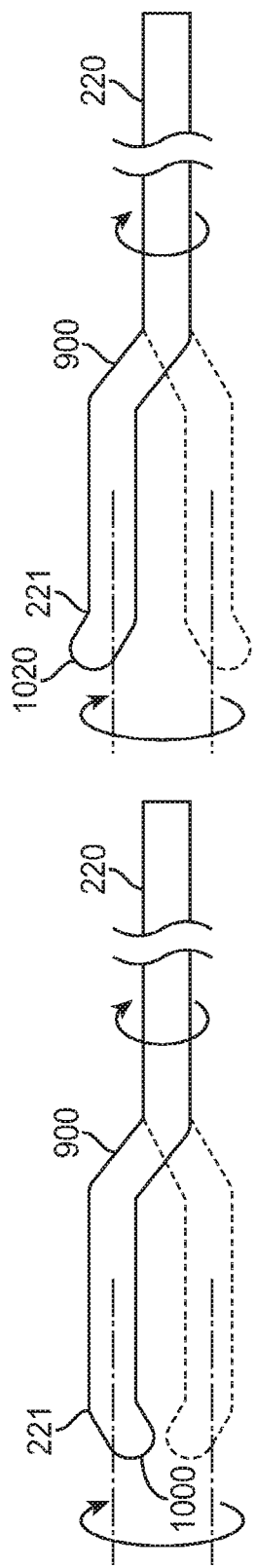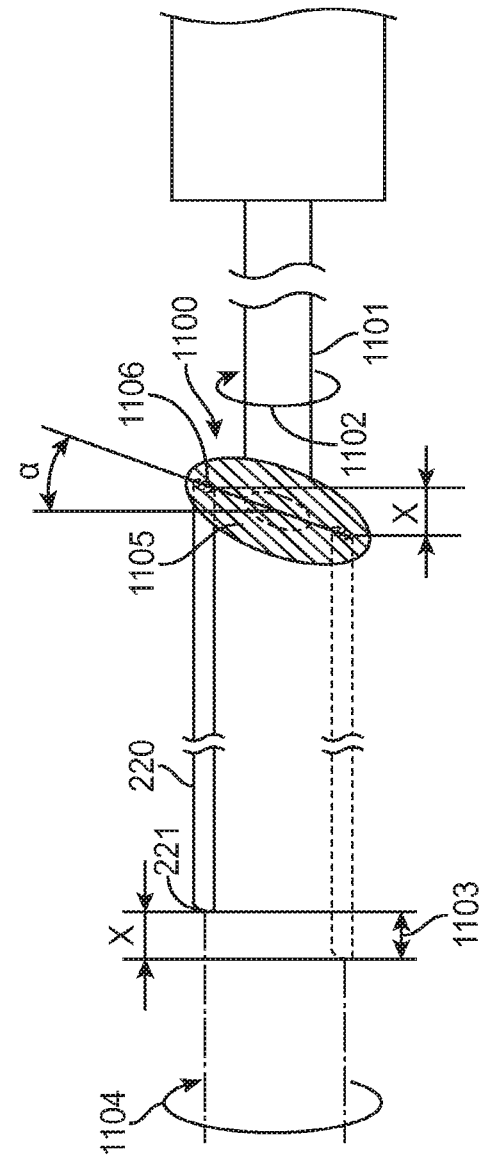

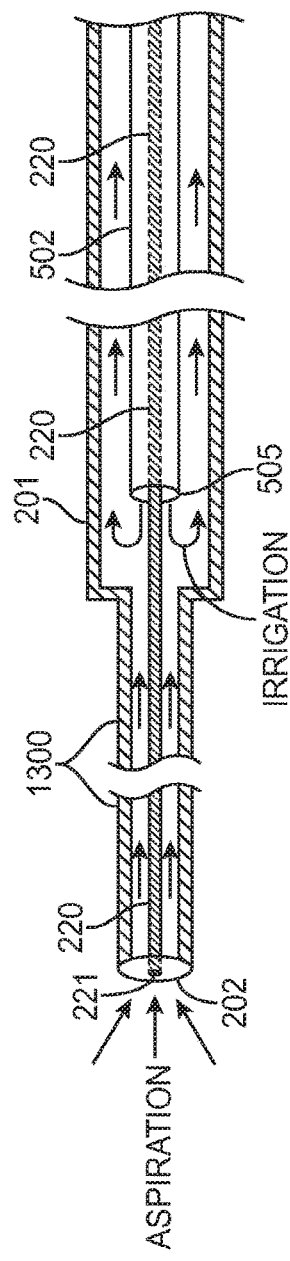
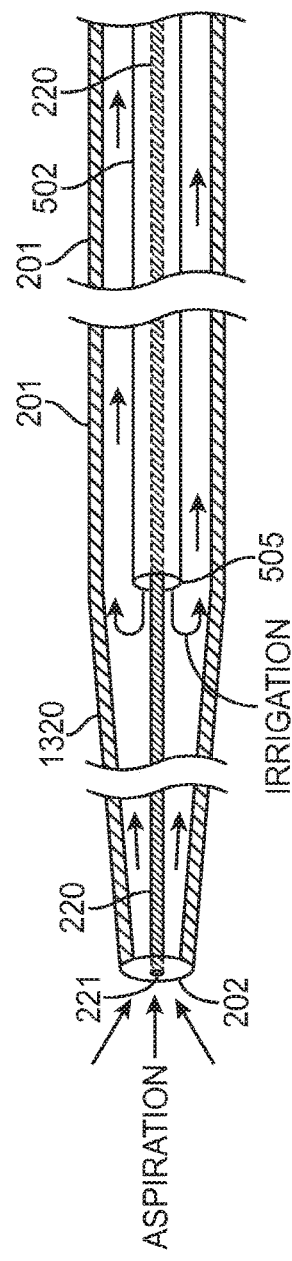
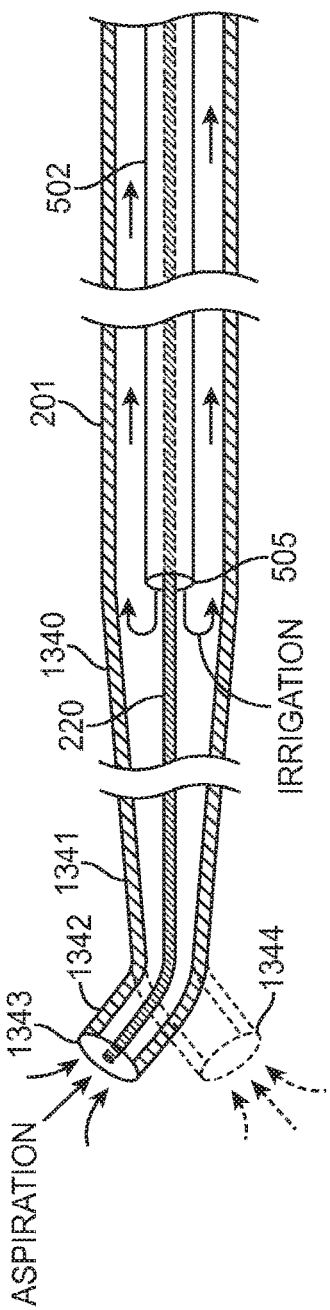
FIG. 13A
FIG. 13B
FIG. 13C

METHODS AND DEVICES FOR REMOVING OBSTRUCTING MATERIAL FROM THE HUMAN BODY

CROSS-REFERENCE TO RELATED APPLICATION(S)

This application is a continuation of U.S. application Ser. No. 14/212,987, filed Mar. 14, 2014, entitled "Methods and Devices for Removing Obstructing Material from the Human Body," which is a continuation-in-part of U.S. application Ser. No. 13/870,777, filed Apr. 25, 2013, entitled "Intracerebral Hemorrhage Treatment." The entireties of both of the above-referenced patent applications are herein incorporated by reference for all purposes.

FIELD OF THE INVENTION

The field of the present application pertains to medical devices. More specifically, the present application is related to systems and methods for intracerebral hemorrhage treatment and removal of obstructing matter from the other parts of human body.

DESCRIPTION OF RELATED ART

Spontaneous intracerebral hemorrhage (ICH) bleeding accounts for approximately 10-15% of all stroke cases, with reports of 37,000 to 52,400 cases annually in the U.S. alone. ICH has long been associated with high rates of morbidity and mortality. According to a ten-year study, 34% of patients with ICH die within 7 days, and 50% die within 30 days. For patients who survive up to a year, only an estimated 20% are expected to be functionally independent. In up to 45% of ICH cases, blood flows into the ventricles of the brain, resulting in Intraventricular Hemorrhage (IVH). This condition is associated with a much poorer prognosis and a death rate of up to 70%.

As blood spreads from the point of origin of an ICH through the brain, it can cause infections, high fever, headaches, vomiting, increased blood pressure, hyperglycemia (even in patients without diabetes), seizures, decreased consciousness, blood clots, and events related to blood clots. Prolongation of hospitalization, paralysis, morbidity, and mortality often result. In addition, expansion of the hematoma and resulting edema often cause brain damage. Hematomas also expand over time in many cases of ICH. For every 10% increase in hematoma growth, there is a 5% increase in mortality rate. Edema is characteristic of fluid collection within the vicinity of the hematoma. Products of edema can lead to neuronal death as it expands from the origins of the hematoma to the tissues beyond. Hematoma expansion, with or without edema, is a huge factor in a patient's outcome. Fatality rates are high in this patient population.

Treatment choices for ICH are limited, and the effectiveness of currently available treatment methods is also limited. Interventions in ultra-early hemostatic therapy are ideally useful in minimizing the continuing growth of the hematoma. The use of recombinant activated factor VII (rFVIIa), an approved drug for hemophiliac patients has been reported to reduce bleeding and hematoma growth when administered at the early stages of ICH (within 4 hours). There was a slight increase in thromboembolic events in the treatment group, however, compared to the placebo group. Also, patients given high doses were at an increased risk of IVH, especially in the higher dose groups. Though rFVIIa used within four hours of ICH minimizes the growth of hematoma, it is limited by its inability to remove hematoma once growth has stopped, and is not recommended at present for routine use.

For ICH, thrombolytics are not recommended to be used alone, and are currently being investigated for use in conjunction with aspiration and other surgical techniques. In patients with IVH, procedures traditionally included the use of a ventricular catheter to drain the blood. However, the use of a catheter alone is not recommended due to lack of catheter patency and slow removal of intraventricular blood. Thus, the administration of fibrinolytic agents as an adjunct to ventricular catheter use is being investigated.

For patients with hematomas resulting from ICH, the role of surgery in improving outcome is uncertain, as hematoma locations vary widely, and the damages from surgery may be greater than those from the hematoma. Patients with small hemorrhages are typically observed and medically managed. Those patients with cerebellar hemorrhage who have brainstem compression and rapidly deteriorating neurological status are recommended to undergo surgical evacuation of the hematoma as soon as possible. The use of craniotomy and surgical removal techniques in other cases are still uncertain.

The STICH trial compared early surgery with initial conservative treatments for patients with ICH. At 6 months, 26% of patients undergoing surgery had favorable outcomes compared to 24% of the initial conservative treatment. Mortality at 6 months was 36% for surgery compared with 37% for conservative treatment. None of these values reached significance, and no overall benefit was demonstrated for early surgery over conservative treatment. Although surgery for ICH is currently undergoing further study, these early data from STICH are not very promising.

Another ICH treatment option under investigation is the use of minimally invasive surgery (MIS) in hematoma evacuation. In theory, the use of MIS would reduce time of surgery, reduce tissue damage, and be performed with local anesthesia. There are several methods under the umbrella of MIS, including endoscopic and stereotactic techniques with or without thrombolysis. In a typical endoscopic surgery, the hematoma is accessed through a burr hole incision, in which a working channel is created into the center of the hematoma, and subsequent action is taken for hematoma removal through this channel. MIS stereotactic procedures involve the use of an image-guided system to precisely locate and visualize the hematoma which is then removed with a combination of aspiration and possibly a lytic drug. The disadvantage in the use of stereotactic techniques lies in the longer procedure times for the patients. Even so, studies have demonstrated a trend of increased clot removal and decreased mortality in subjects treated within 12-72 hours for both stereotactic and endoscopic options. However, functional improvement has not been consistently demonstrated, and clot resolution is highly dependent on where the catheter is positioned.

A number of inventions have been described in the general area of treating intracranial or intracerebral hemorrhage. Examples include U.S. Pat. No. 8,366,620, entitled Methods and apparatus for intracranial ultrasound delivery, and U.S. Patent Application Publication Nos.: 2012/0330196, entitled Methods and Apparatus for Removing Blood Clots and Tissue from the Patient's Head; 2012/0179073, entitled Ischemic Stroke Therapy; 2012/0078140, Method and Apparatus for Removing Blood Clots and Tissue from the Patient's Head; 2011/0319927, Methods and apparatus for removing blood clots from intracranial aneurysms; 2011/0313328, entitled Methods and apparatus for dissolving blockages in intracranial catheters; and 2011/0160621, entitled Methods and apparatus for dissolving intracranial blood clots.

In summary, ICH is a very common cause of death and disability with no ideally effective treatment currently available. Thus, there is a significant need for improved methods and systems for treating ICH. Ideally, such methods and systems would provide effective reduction of morbidity and mortality rates associated with ICH. Also ideally, such methods and systems would be relatively easy to use and inexpensive to manufacture, so that they could be made readily available in emergency medicine settings. At least some of these objectives will be met by the embodiments described below.

There are many clinical approaches for removing obstructing material, unwanted matter from human body, many of which are performed surgically when the treatment site is accessed directly through a surgical incision. However, in recent years a variety of catheter devices have been developed for endovascular and outside endovascular removal of obstructive matter, such as blood clots, thrombus, atheroma, plaque and the like. For example, a catheter device is inserted into a blood vessel at an access site, and is then advanced through the vessel lumen until the treatment site is reached. These techniques may employ various devices to fragment the unwanted clot or tissue from blood vessels such as rotating baskets or impellers as described in U.S. Pat. Nos. 5,766,191 and 5,569,275, cutters as described in U.S. Pat. No. 5,501,694 and high pressure fluid infusion to create a Venturi effect as described in U.S. Pat. No. 5,795,322. Other devices rely on the principles of the Archimedes type screw, such as a one-piece solid machined screw to break up and/or remove clot. The U.S. Pat. No. 5,556,408 describes an atherectomy cutter employing a vacuum source for removal of loose stenotic material and other debris from a vessel. Removal of thrombus by a rotating core wire on a drive shaft is described in the U.S. Pat. No. 5,695,507. Fragmentation and removal of tissue using high pressure liquid is described in the U.S. Pat. No. 5,795,322. The U.S. Pat. No. 4,923,462 describes a coiled wire coated with Teflon and used as a drive shaft to rotate a catheter. Furthermore, the U.S. Pat. No. 5,334,211 describes a coiled guidewire used to stabilize an atherectomy device. Atherectomy catheters with rotating helical pumping elements are described in the U.S. Pat. Nos. 4,732,154; 4,886,490; 4,883,458; 4,979,939; 5,041,082; 5,135,531; 5,334,211; 5,443,443; and 5,653,696. A rotary thrombectomy catheter having an inner helical blade is commercially available under the trade name Straub Rotarex® from Straub Medical AG, as described in a brochure with a copyright of August 1999. Use and construction of the Straub Rotarex® also appears to be described in Schmitt et al. (1999) Cardiovascular Interventional Radiology 22:504-509 and in U.S. Pat. Nos. 5,876,414 and 5,873,882. Other patents of interest include U.S. Pat. Nos. 4,737,153; 4,966,604; 5,047,040; 5,180,376; 5,226,909; 5,462,529; 5,501,694; 5,569,275; 5,630,806; 5,766,191; 5,843,031; 5,911,734; 5,947,940; 5,972,019; 5,376,100; 5,569,275; 7,037,316; 7,179,269; 7,235,088; 7,666,161; 7,763,010; 7,842,006; 7,842,055; 7,938,820; 7,942,852; 8,062,317; 8,414,543; 8,414,543; 8,535,290 and 8,545,447, as well as published PCT applications WO 99/56801, WO 99/56638, and WO 98/38929. Motor drive units for catheters and other devices are described in U.S. Pat. Nos. 4,771,774 and 5,485,042.

In many instances, the luminal treatment techniques include infusing the vessel or treatment site with fluid (saline, thrombolytic agent or therapeutic drug) to assist in breaking up the clot or tissue into a particle size that can then be aspirated through a lumen of the treatment device or using a secondary catheter hooked up to a source of vacuum/suction. Depending on the method of fragmentation and the consistency of the clot or tissue, the particle size can vary. If the material is not thoroughly fragmented, the larger particles can build up in the catheter and block the aspiration lumen.

While these catheters and techniques have been well known and are fairly successful, there is a need for improved devices for more efficiently disrupting and evacuating fragmented material from the vessel or body lumen in order to overcome the difficulties of continued fluid infusion and material build up that blocks the aspiration lumen. Furthermore, it would be desirable to have devices that allow faster aspiration and removal of larger particles of fragmented material, thereby reducing procedure time. Preferably, such improved devices will have a low profile to enable percutaneous, minimally invasive and surgical use, and will be flexible and torqueable to enable their use in areas difficult to access. Furthermore, such devices can be designed to be placed over a guidewire and will be structured to mechanically translate and transport the fragmented material by directly aspirating it through the device shaft. Optionally, the devices should include mechanisms for infusing liquids to further facilitate disruption of the occlusive materials.

BRIEF SUMMARY

Example embodiments described herein have several features, no single one of which is indispensable or solely responsible for their desirable attributes. Without limiting the scope of the claims, some of the advantageous features of some embodiments will now be summarized.

In one aspect, a method for removing a blood clot from a cranium of a patient may involve: forming an opening in the patient's cranium; advancing an elongate blood clot removal device through the opening into the cranium; positioning a distal end of the clot removal device at or near the clot; rotating a rotating member of the clot removal device at or near the distal end of the clot removal device to at least partially break up the clot; and removing the at least partially broken up clot from the cranium through the clot removal device. In some embodiments, the rotating member may be rotated at a speed of between about 10 revolutions per minute and about 500,000 revolutions per minute. In some embodiments, the blood clot may be located underneath dura mater of the patient's brain, and the elongate clot removal device is advanced through the dura mater.

In some embodiments, the blood clot resides in an epidural or subdural space of the patient's cranium. In some embodiments, the blood clot is a result of an intracerebral hemorrhage. In some embodiments, the method may include, before the advancing step, placing an introducer device in the opening in the cranium, where the clot removal device is advanced into the cranium through the introducer device. Some embodiments may include, before the advancing step, placing a trocar in the opening in the cranium, where the clot removal device is advanced into the cranium through the trocar. Any embodiments may also optionally include monitoring the placement of blood clots removal device and/or trocar using a monitoring device such as but not limited to an image guided navigation system, a computed tomography scan, ultrasound and endoscopes.

The clots removal device advancement to the treatment location may be monitored by any suitable visualization apparatus including but not limited to CT (Computed Tomography), MRI (Magnetic Resonance Imaging), radiographic technologies or Optical Coherence Tomography (OCT). The clot removal device may be used with endoscope systems. Some endoscopes also include working channel where the blood clot removal device can be advanced to the treatment area. Also, a mini camera for a distal visualization may be provided as an integral part of the blood clots removal device. In recent years, neuro guided-navigational systems are gaining a lot of popularity in neurosurgery and are frequently used to navigate, position and immobilize neurosurgery devices and tools inside the skull. Such access device can be a part of a stereotaxis frame or it can be frameless and therefore directly secured to the skull. The device's relative location can be also tracked in the skull based on previously obtained MM, CT or ultrasound images by using reflective elements mounted on the proximal end of the clot removal device system and IR light sources that can locate the specific position and orientation of the cranium.

The present invention also relates to medical apparatus and methods and more particularly to devices and methods for removal of unwanted tissue such as thrombus, atheroma, fluid, polyps, cysts or other obstructive matter from endovascular system including arteries, veins, previously implanted stents, grafts, shunts, fistulas and the like, as well as, body organs, ureters, bile ducts, fallopian tubes or localized tumors.

In some embodiments, the method may further involve delivering at least one pharmacologic agent to the blood clot using the clot removal device. For example, the agent may include, but is not limited to, tissue plasminogen activator, tPA, BB-10153, rTPA, Urokinease, Streptokinase, Alteplase, Desmoteplase, other blood clot reducing agents, aspirin, Clopidorgel, Ticclopidine, other antiplatelet agents, Abciximab, Tirofiban, Eptifibatide, and/or other GIIb/IIIa inhibitors. In some embodiments, the method may further involve delivering a sterile solution of sodium chloride into the cranium through the clot removal device.

In some embodiments, removing the clot involves applying suction to the clot via the clot removal device. In an alternative embodiment, removing the clot may involve allowing the clot to gravitationally drain via the clot removal device.

In another aspect, a method for removing a blood clot from a cranium of a patient may involve advancing an elongate blood clot removal device through an opening into the cranium, positioning a distal end of the clot removal device at or near the clot, rotating a rotating member of the clot removal device at a speed of between about 10 revolutions per minute and about 500,000 revolutions per minute to at least partially break up the clot, and applying suction to the clot via the clot removal device to remove the clot from the cranium.

In various embodiments, positioning the distal end of the clot removal device may involve positioning the distal end near the clot, immediately adjacent the clot, contacting the clot and within the clot.

Some embodiments of the method may further involve cooling brain tissue during the rotating step. For example, cooling brain tissue may involve cooling the patient's neck, cooling the patient's head and/or cooling the patient's body.

In another aspect, a system for removing a blood clot from a cranium of a patient may include: an elongate clot removal member having an inner lumen and an outer diameter along at least a distal portion of the clot removal member of between about 0.5 millimeter and about 5 millimeters; a rotating member housed within the lumen of the clot removal member and configured to rotated within the clot removal member at a rate of between about 10 revolutions per minute and about 500,000 revolutions per minute; and a vacuum source coupled with the clot removal member to generate a vacuum within the lumen.

In some embodiments, the elongate clot removal device may include a rigid distal shaft portion, a flexible proximal shaft portion, and a handle disposed between the distal shaft portion and the proximal shaft and including an aperture in fluid communication with the lumen and configured to be covered with a finger of a user to regulate application of the vacuum. Optionally, the system may further include an introducer device for placing in a burr hole in the cranium to facilitate advancing the clot removal member into the cranium. Also optionally, the system may further include a trocar for advancing through the introducer device into the cranium, where the clot removal member is advanced into the cranium through the trocar.

According to the present invention, improved devices and methods are provided for transporting material between a target site in the body of a patient and a location external to the patient. In some cases, the materials will be transported by methods which will generally be referred to as aspiration. In other cases, the material may be transported from the external location to the target site within the body lumen, which methods will generally referred to as infusion or irrigation. In all cases, the material transport will be enhanced by rotation of a rotational member disposed in a lumen of a device. The rotational member will usually comprise a tubular or solid rotational member having an end extending at least partially within a device and the distal end of the rotational member located inside the device or partially extending beyond the distal end of the device. Thus, rotation of the rotational member will break the material that is aspirated through the device and outside the patient.

For example, the obstructing material removal device of the present invention may be used to infuse thrombolytic and other therapeutic agents and/or aspirate fragmented clot, thrombus, and other occlusive materials in conjunction with angioplasty, atherectomy, laser ablation, embolectomy, atherectomy and other known intravascular interventions.

In one embodiment, a device for removing obstructing matter from a patient include an elongated rotational member having a distal end, and a proximal end connectable to a rotation generating device that is configured to rotate the rotational member along its longitudinal axis. An internal irrigation catheter is at least partially surrounding the rotational member. An aspiration catheter is positioned around the internal irrigation catheter and the rotational member and adjacent to the distal portion of the rotational member. The aspiration catheter may have a guidewire lumen for a better navigation to the treatment location. The rotating rotational member breaks up obstructing matter and facilitates its aspiration through the aspiration catheter outside the patient. The rotational member may rotate clockwise, counter clock wise or both and can be made of a single rotating member, multimember rotating members or both. In addition, the rotational member can be configured to translate proximally and distally within the device to aid in breaking up the clot and preventing the device from clogging during aspiration.

In various embodiments, the device for removal obstructive material can operate in rotational continuous mode, pulse mode and a combination of both. In some other embodiment rotations can be modulated. Modulation of rotations may include speed modulation through electronic adjustment of voltage, current, as well as, pulse parameters (ON/OFF time) or any combination of all.

In another embodiment, a device for removing obstructing matter from a patient includes a rotational member rotating around its primary axis, which also creates angular motion on the distal end of the rotating member Angular motion includes rotational motion of the rotational member which is off-set from the primary longitudinal axis of the rotational device.

In another embodiment, a device for removing obstructing matter from a patient includes a rotational member having a bend that changes longitudinal axial motion of the rotational member to angular motion. Such bend may be located along the length of the rotational member. If such bend or deformation is located on the distal end of the rotational member, it will rotate the distal end of the rotational member in angular motion while the proximal portion of the rotational member will mostly rotate along its primary longitudinal axis.

In yet another embodiment, a device for removing obstructing matter from a patient include a cam, an irregularly shaped projection located on a rotating shaft of the motor or on the rotational member that changes rotary motion into a reciprocating back and forth motion of the rotational member along its longitudinal axis.

In yet another embodiment, a device for removing obstructing matter from a patient includes a rotational member that is connected to a motion converter that changes its longitudinal motion in to a reciprocal and angular motion. Such converter can be located on the rotational shaft of the motor or on the rotational member. In such embodiment, the rotational member rotates in angular motion, while simultaneously; the rotational member is reciprocating back and forth.

In another embodiment of the present invention, the distal end of device for obstructive material removal has a change in cross sectional area, narrowing or distal taper to increase fluid aspiration velocity into the device. In addition, a bend or deflection is implemented on the very distal end of the device to cover a larger treatment area and create more angular motion.

Some embodiments of the present invention include advancing a device for obstruction material removal to the treatment site in conjunction with appropriate positioning of the device at the treatment site. Advancing the device may be accomplished by conventional approaches either using additional positioning catheter such as guiding catheter or sheath and/or with a guidewire. Guidewire-assisted methods may include any approach, such as over-the-wire or monorail deployment.

As noted above, some embodiments may include repeated applications, or multiple applications at the same site, or at another portion of a treatment site. Thus, for example, embodiments of the devices and methods may include repositioning the device for removal of obstructive material and repeating the step of activating the device. Positioning the device for obstructive matter removal at the target site may include positioning the device nearby the target site, or it may include contacting a healthy tissue at the treatment site.

Another aspect of the present invention may include plaque reduction to increase the patency of the afflicted vessel as a stand-alone intervention directed toward increasing vessel patency, or such treatments may be done in conjunction with other interventional approaches.

In various other embodiments of the present invention, removing obstructive material further include performing therapeutic, diagnostic, supporting or drug delivery procedure before, during or after obstructive material removal from the patient.

As used herein, "rotational member" and "rotating member" of the device for removal of obstructive material from the patient refer to same component.

As used herein, "obstructive matter" and "obstructive material" refer to same subject.

These and other aspects and embodiments will be described in further detail below, in reference to the attached drawing figures.

BRIEF DESCRIPTION OF DRAWINGS

Certain preferred embodiments and modifications thereof will become apparent to those skilled in the art from the detailed description below having reference to the figures that follow.

FIG. 2 is a side, cross-sectional view of a blood clot removal device that is part of the system of FIG. 1, according to one embodiment;

FIGS. 3A-3F are side views of six alternative embodiments of distal end configurations of rotating members of the blood clot removal device of FIGS. 1 and 2, according to various alternative embodiments;

FIGS. 4A-4D are side, partial cross-sectional views illustrating a method for removing one or more clots from a cranium, according to one embodiment;

FIG. 8A-D show a rotating member with several different configurations;

FIG. 9 shows a rotating member having a bend on the distal portion;

FIG. 10A-B show a rotational member having a primary bend on the distal very end, and an adjacent secondary bend;

FIG. 11A-B show a converter that transforms circular rotations of the motor shaft into angular rotations and reciprocating motion of the rotational member;

FIG. 13A-C show several configurations of the distal end of the device for obstructive material removal having decreased cross sectional area on the distal end.

DETAILED DESCRIPTION

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments. However, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

In the following description, embodiments will sometimes be described for use in treating intracerebral hemorrhage (ICH), which is one type of intracranial hemorrhage. This description related to ICH should not be interpreted as limiting any particular embodiment or this application as a whole to ICH treatment. In fact, many embodiments of the systems and methods described herein may be applied to either ICH or to other forms of intracranial hemorrhage. Therefore, unless an embodiment or feature is described specifically as applying only to ICH, any embodiment or feature may be used in treating ICH and/or other types of intracranial hemorrhage.

Figure 1:
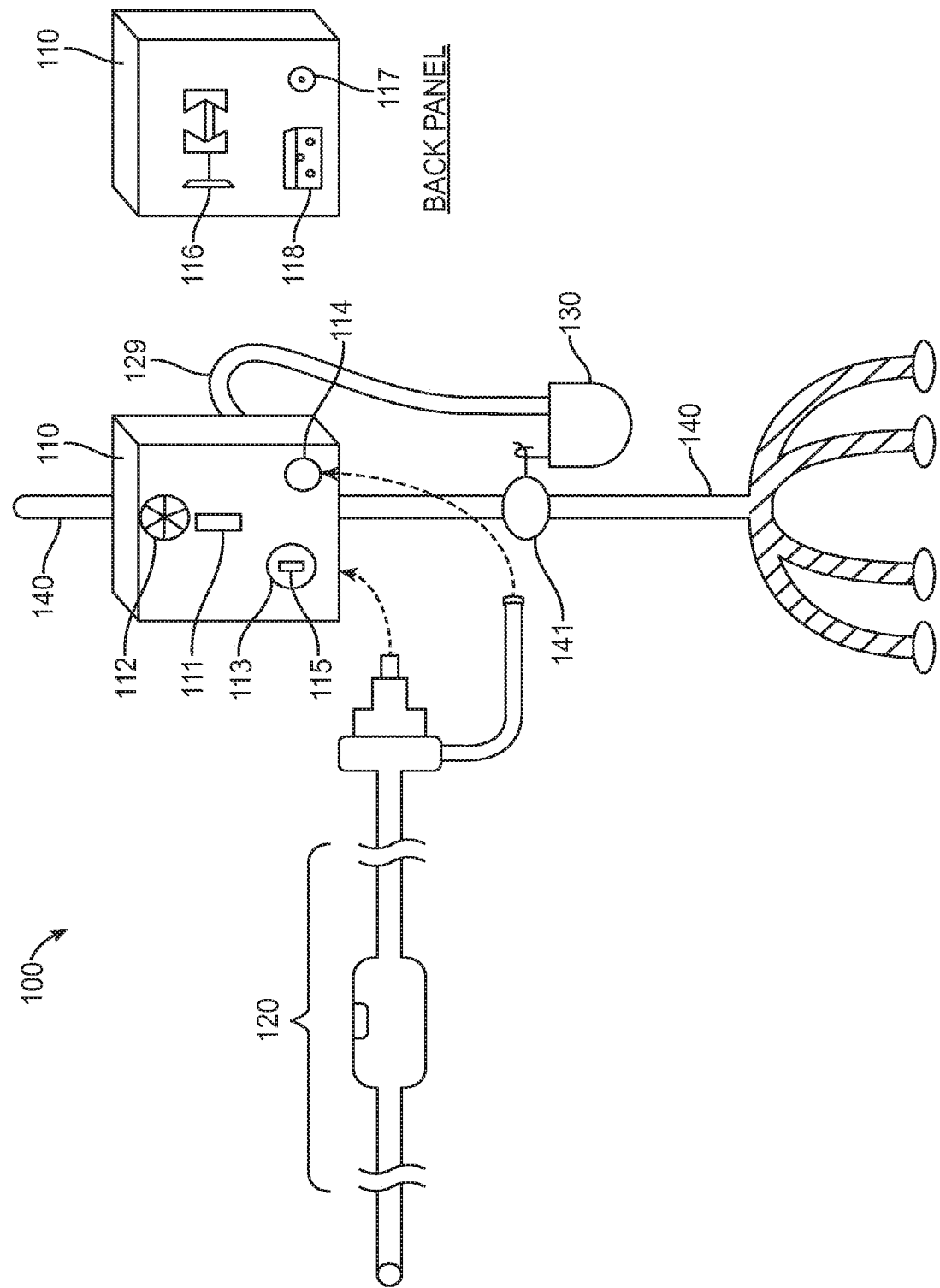
FIG. 1 is a perspective view of an intracerebral hemorrhage treatment system, according to one embodiment.

Referring now to FIG. 1, one embodiment of an ICH treatment system 100 (or "ICH removal system") may include a hardware box 110, a blood clot removal device 120 (or "catheter"), and a blood clot collection bag 130. The hardware box 110 may be placed on an IV pole 140, for example, or may be attached to any other suitable support device in alternative embodiments. In various alternative embodiments, the ICH system 100 may include fewer components or additional components. For example, in one embodiment, the system 100 may not include the collection bag 130, and some other type of collection device may be used, such as any suitable, currently available device for collecting blood or blood clots. In other embodiments, at least one introducer device may be included with the system 100. For example, an introducer and/or a trocar may be included in the system 100 in some embodiments. Therefore, the embodiment of the system 100 illustrated in FIG. 1 is provided for exemplary purposes only and should not be interpreted as limiting the scope of the system.

The hardware box 110 may house an electrical motor and one or more vacuum pumps, neither of which are pictured in FIG. 1, since they are housed within the box 110. The front panel of the ICH hardware box 110 may include an ON/OFF switch 111 for activating the vacuum pump and electrical motor, a vacuum level indicator 112 for indicating the vacuum level applied to the blood clot removal device 120, a rotational inlet 113 for attaching the blood clot removal device 120 to the hardware box 110, and an aspiration inlet 114 for attaching aspiration tubing 206 (FIG. 2) of the blood clot removal device 120 to the hardware box 110 (vacuum pump inside the hardware box 110). In general, the box 110 contains a source of vacuum force and a motor for moving a rotating member 220 (FIG. 2) in the blood clot removal device 120. The box 110 may either contain or be attachable to a power source. For example, in some embodiments, the box 110 may be attached to an electrical cable (not shown) for plugging into a wall outlet. In other embodiment, the box 110 may include one or more disposable or rechargeable batteries.

Attachment of the blood clot removal device 120 to the hardware box 110 connects a proximal end 222 of the rotational member 220 (FIG. 2) located inside the connector 208 of the blood clot removal device 120 (FIG. 2) to a slot 115 located on the motor shaft inside the inlet 113. The slot 115 rotates when the motor is activated and thus rotates the proximal rotational member 222. In various alternative embodiments, the inlet 113 and/or the slot 115 may have different configurations. For example, although this description focuses on a clot removal device 120 having a proximal rotating member 222, in alternative embodiments any suitable alternative form of moveable member may be substituted. For example, in some embodiments a member that translates, oscillates, vibrates and/or the like may be substituted for the proximal rotating member 222. Thus, neither the blood clot removal device 120 nor the hardware box is limited to rotational movement. Generally, a blood clot, blood and/or other tissue that may be removed from the head or other part of the body, in various embodiments, is aspirated by the vacuum pump (not shown) located inside the hardware box 110 through the blood clot removal device 120 (FIG. 2) and a collection tube 129 to the collection bag 130. The collection bag 130 may be attached, for example, to a hook 141 located on the pole 140.

In one embodiment, a back panel of the hardware box 110 may include an IV pole mounting clamp 116, an aspiration outlet 117, and an electrical inlet 118. The aspiration outlet 117 is used for coupling the collection tube 129 with the box 110. The electrical inlet 118 is used for connecting an electrical cord for attachment to a wall outlet or other electrical power source. In various embodiments the rotating proximal member 222 can be directly affixed to an electrical motor, and in such configuration the electrical motor within an enclosure would become an integral part of the device 120 (not shown). In one embodiment the electrical motor can be directly connected via electrical cable to the power source either in the box 110 or to the electrical outlet on the wall. In another embodiment, energy source such as batteries may be included with the motor in the enclosure. Irrigation inlet and aspiration outlet may also be attached to the box 110, or independently to any suitable irrigation pump and aspiration pump available.

With reference now to FIG. 2, the ICH blood clot removal device 120 may generally include three main portions—a rigid distal tube 201, a handle assembly 210, and a proximal shaft 203. One continuous inner lumen 212 may extend through most or all of the length of all three portions. Some embodiments may include two or more lumens. In various embodiments, the rigid distal tube 201 may have a length of about 10-45 cm, and more preferably about 15-30 cm, and an outer diameter of about 0.5-5 mm, and more preferably about 1-3 mm. The rigid distal tube 201 is rigid relative to the proximal shaft 203 and has an open distal end 202 (or a distal end with one or more openings) for aspirating blood clots, blood, etc. into the lumen 212. The rigid distal tube 201 may also be referred to as a "wand," and it will be sufficiently rigid to allow a physician user to push it to a desired location in the brain, but it will also have an atraumatic distal end 202 configured to minimize damage if it contacts a vital structure. The rigid distal tube may be made of any suitable, relatively rigid material, such as but not limited to a metal, metal alloys including superelastic Nitinol or polymer. Also, in some instances the rigid distal tube can be made of flexible materials as seen in vascular catheter devices.

Extending through the lumen 212 is a rotating member 220, which rotates rapidly at or near with distal end 202 to help break up blood clots as they enter the lumen 212. The rotating member 220 may include a shaped proximal end 222, configured to couple with a driver/motor for rotating the rotating member 220. The rotating member 220 will be described further below.

The handle assembly 210 provides a holding place for a user to hold the device 120 and manipulate the distal tube 201. The handle assembly 210 also provides a way for the user to regulate the vacuum level applied to the distal end 202 of the tube 201. The handle assembly 210 may include an aperture 211 that is in fluid communication with an inner lumen 212. If the aperture 211 is open, as shown, vacuum applied to the catheter 120 from the hardware box 110 brings in air from outside of the handle 210 through the aperture 211. Thus, vacuum applied at the distal end 202 of the catheter tube 201 is minimal or significantly reduced when the aperture 211 is open. If the aperture 211 is closed, such as by covering it with a finger, during removal of a blood clot from inside a cranium, a maximum vacuum will be applied to the distal end 202 of the tube 201. The handle 210 can be made of metal, metal alloy including superelastic Nitinol, polymer, rubber or a combination thereof.

The proximal shaft 203 may be attached to the handle 210 or may be a proximal extension of the handle 210. The proximal shaft 203 is a typically a single lumen polymer tube. A sealed insert 204 connects the proximal shaft 203 with a connector 208. The sealed insert 204 may include an outlet 205 for connecting to a vacuum tube 206 and a sealing member 207 for preventing air from entering the proximal shaft 203 from the proximal end of the device 120. Thus, the sealed insert helps ensure maximum aspiration pressure on the distal end 202 of the tube 201 by preventing air leakage. The vacuum tube 206 may be connected to the aspiration inlet 114 located on the front panel of the box 110 (FIG. 1).

The proximal connector 208 is configured to enable attachment of the blood clot removal device 120 to the inlet 113 inside the hardware box 110. The rotating member 220 extends longitudinally through the blood clot removal device 120 from the proximal connector 208 to the distal end 202. The rotating member 220 has a distal end 221 located within the tube 201 at or near the tube's distal end 202. The proximal end 222 of the rotating member 220 extends out of the proximal connector, in this embodiment. The proximal insert 222 is configured for easy connection with the slot 115 located on the motor shaft inside the rotational inlet 113 of the box 110 (FIG. 1). The distal end 221 of the rotational member is configured to macerate blood clots when rotated and during aspiration of blood clots into the distal end 202 of the tube 201. Such chopping up of blood clots under vacuum allows for an effective and continuous removal of blood clots.

Referring now to FIGS. 3A-3F, six alternative embodiments of distal ends 221 of the rotating member 220 are illustrated. These embodiments are by no means the only configurations that may be employed, but are merely provided for exemplary purposes. The embodiments of the distal end shown in these figures are a ball shaped distal end 301 (FIG. 3A), a flat/circular distal end 311 (FIG. 3B), a bent distal end 321 (FIG. 3C), a coiled distal end of any pitch 331 (FIG. 3D), a flat, proximal deformation 341 (proximal to the extreme distal end of the rotating member 220—FIG. 3E), a basket 351 (FIG. 3F) and sinusoidal shape (not shown). Any configuration of the rotational member 220 that crushes, macerates, disintegrates or otherwise at least partially breaks up a blood clot at the distal end 202 of the tube 220 or facilitates mashing blood clots along the entire length of the ICH removal catheter 120 is suitable for this application.

Figure 4D:
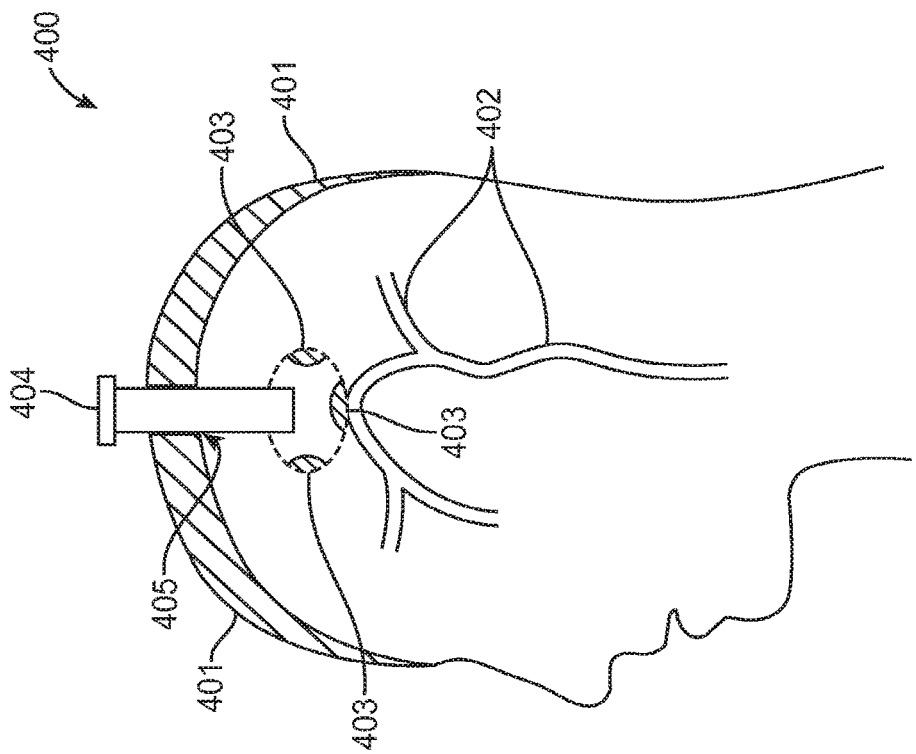

FIGS. 4A-4D illustrate a method for removing a blood clot from a cranium, according to one embodiment. FIG. 4A shows a cross-sectional view of the human head 400, including the cranium 401 (or "skull"), a few main intracerebral vessels 402 and a blood clot 403 (or collection of multiple blood clots). For purposes of this description, no distinction is made between removing one blood clot and removing multiple blood clots from the brain. In various embodiments, the systems and methods described herein may be used for removing one clot, multiple clots in one location or multiple clots in different locations.

In some embodiments, a first step of a method for treating ICH may include forming an opening in the cranium. The opening is typically a burr hole 405, which is a standard and commonly performed access opening through a skull. However, it can also be any other aperture often used for mini-craniotomy. In some embodiments, the burr hole 405 or some other opening may have already been formed before the method is begun, for example by some other physician for another purpose. In either case, the next step in some embodiments may be to position an introducer 404 through the burr hole 405 or other aperture in the skull 401. A distal end of the introducer 404 may be positioned near to or inside the blood clot(s) 403. Positioning of the introducer 404 can be achieved with the use of any suitable devices or currently available technology for helping position a device, including but not limited to ultrasound and neuro-navigational systems.

Referring to FIG. 4B, a next step of the method may involve advancing a trocar 500 through the introducer 404. When a distal end 501 of the trocar 500 is positioned at, within or near the clots 403, the introducer distal end may be slightly retracted proximally away from the blood clots 403 to allow trocar distal end 501 a better view of the clots 403. The trocar 500 may be any suitable, currently available or yet to be invented trocar. Typically, the trocar will include visualization and working channels, and many different trocars are currently available for use in neurosurgical procedures. Examples of companies providing trocars include, but are not limited to, Storz (Hopkins 6° Telescope w/ Angled Eyepiece), Aesculap (Minop Intraventricular Neuroendoscopic System) and Adeor (Haematoscope).

In some embodiments, the trocar 500 may be advanced into the cranium 401 and positioned at or near blood clots 403 without use of an introducer 404. In other words, the introducer step described in reference to FIG. 4A may be skipped in some embodiments.

Figure 4C:
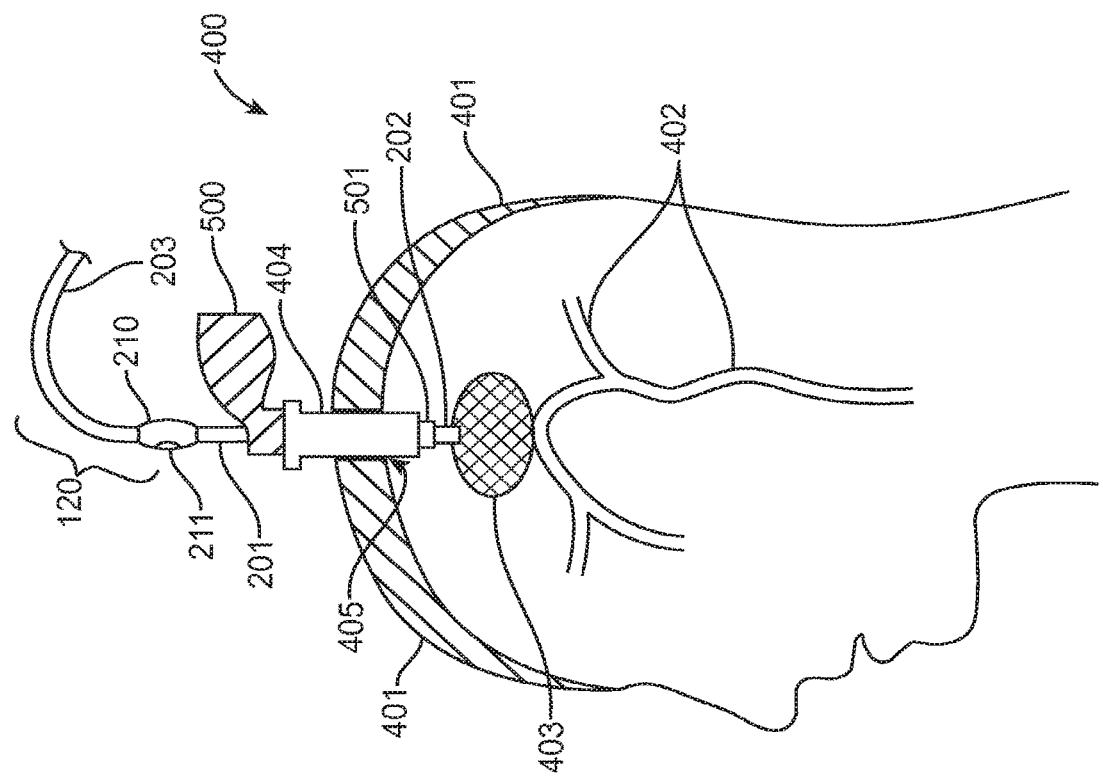

Referring now to FIG. 4C, the next step in one embodiment may involve advancing the blood clot removal device 120 into the cranium 401. In this embodiment, the blood clot removal device 120 is advanced through the trocar 500, which is advanced through the introducer 404. The distal tube 201 is positioned through the working channel of the trocar 500. The trocar 500 has a visualization feature (small camera) located at or near its distal end (not shown) that allows the physician to observe the distal end 202 of the tube 201 in relation to blood clots 403. When the distal end 202 of the tube is in a desired location near to, at or within the clot(s), the physician may activate the ICH removal system 100 by turning switch 111 (FIG. 1) to the ON position. When system 100 is activated, aspiration and rotation of the rotating member 220 (FIG. 2) begin. However, the system will be unable to remove blood clots 403 until the aperture 211 on the handle assembly 210 is covered by the physician's finger. When the aperture 211 is closed, blood clots 403 will be suctioned toward the aperture in the tube 201, thus causing the rotating member 220 to macerate the blood clots 403. The macerated clots 403 continue to be suctioned proximally through the clot removal device 120 and eventually exit the device 120 and proceed through the vacuum tube 206 into the collection bag 130.

FIG. 4D illustrates the same human head as that shown in FIGS. 4A-4C, after removing blood clots 403 and removing the trocar and the catheter. It is common to such procedures that residual blood clots 403 are left in the treatment area. Some of these blood clots maybe left due to inability to locate and remove them. Other blood clots maybe left to prevent further bleeding and creation of more blood clots. If vessels in the treatment area are bleeding after blood clots removal, one or more conventional tools may be used to cauterize these vessels.

Figure 5:
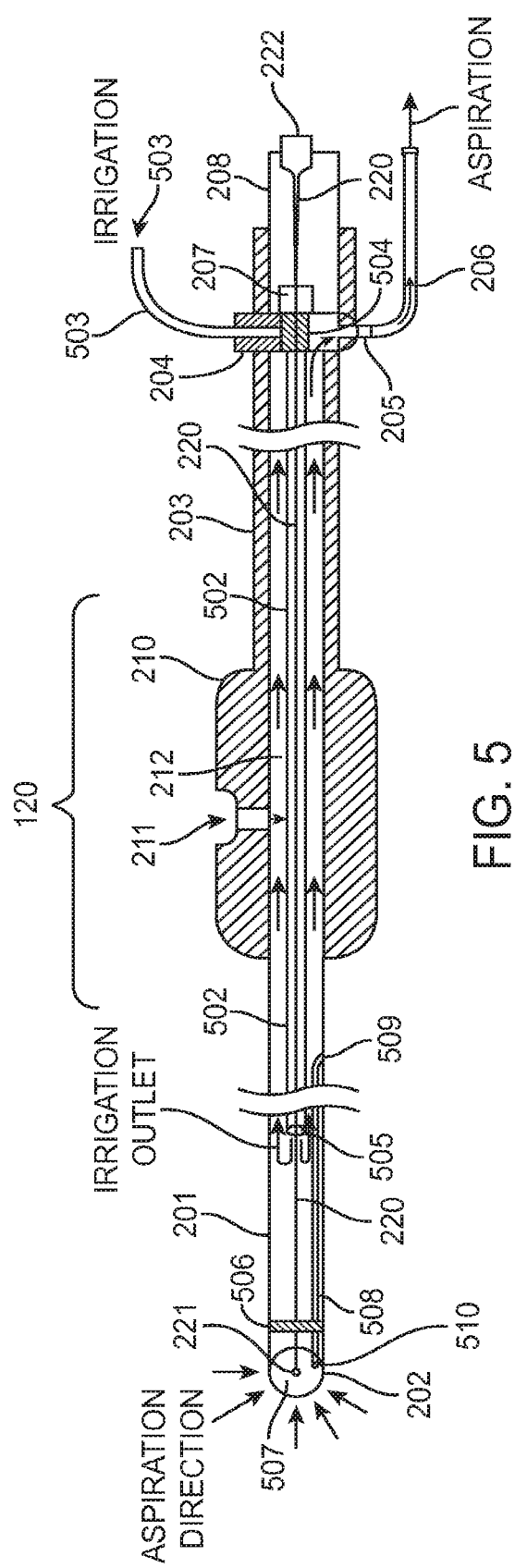
FIG. 5 is a side, cross-sectional view of an obstructing matter removal device that is attached to a separate rotational device as shown in FIG. 1 with addition of an inner catheter for irrigation delivery.

FIG. 5 shows a device for obstructive material removal that utilizes a conventional irrigant, a sterile solution of sodium chloride (NaCl) to facilitate blood clot removal. This device is similar to one shown in FIG. 2 with addition of inner irrigation catheter 502, having an irrigation inlet 503 and a diverting member 504 located inside the sealed insert 204. The irrigation diverting member 504 is constructed such way that irrigant is delivered into irrigation inlet 503, through the diverter 504 and into the irrigation catheter 502 without leaking into the aspiration outlet 205. The irrigation catheter 502 is positioned around the rotational member 220. The irrigation inlet 503 is connected to an irrigation pump which may be a part of the hardware system 110 in FIG. 1 (not shown) or any other irrigation pumps available. It also can be connected to irrigation pressure bag commonly used in operational rooms. The distal end 505 of the irrigation catheter 502 may be terminated at any location along the rotating member 220, preferable within its distal part. During the activation of the system the rotating member 220 rotates axially while irrigation is delivered from the irrigation tube 503 through the diverting member 504 to the distal end 505 of the irrigation catheter 502, and along the rotation member 220. Irrigation liquid vacuumed by the inner aspiration forces inside the aspiration catheter 203 ones it reaches the distal end 505 of the irrigation catheter 502. The rotating distal end 221 of the rotational member 220 changes compliance of material to be removed that is sucked into the distal end 202 by braking material, inducing cracks, creating channels, splitting, tearing, gashing, liquefying or other means such that the modified structure of the material to be removed is further dragged into the aspiration lumen 212 of the device 120, around the irrigation catheter 502 and outside the body. Delivery of irrigant to the distal end 505 of the irrigation catheter 502 provides a liquid flush to further facilitate obstruction material removal and transport under vacuum through aspiration lumen 212 of the probe 201 and the catheter 203. Delivery of irrigation to the distal portion of the device 120 can also be accomplished using a space between outside surface of the irrigation catheter 502 and inside channel of the aspiration lumen 212 (not shown). In such case the inside lumen of the catheter 502 would serve as the aspiration lumen.

In addition to providing irrigation that facilitates obstructive material removal, flow of irrigant around the rotational member 220 may serve as a coolant. While rotating, the rotational member 220 may generate heat, especially around the diverting member 504 and seal insert 204. A continuous flow of irrigant around the rotational member 220 within the diverting member and the seal insert areas will reduce generated heat and increase device reliability and efficacy.

For a better visualization or location of the device 120, a radiopaque marker or electromagnetic sensor 506 maybe located on the distal end of the irrigation catheter probe 201. Also to assure a desirable positioning of the rotating distal end 221 of the rotational member 220, a radiopaque marker or electromagnetic sensor 507 may be located on the distal end of the rotational member 220. In some embodiments the irrigation catheter 203 structure can extend until the distal end 202 replacing the probe 201.

The distal end 221 of the rotational member 220 can be positioned inside the device 212, outside of the device 212, or its location maybe adjusted by the operator as desirable during use. For a better navigation of the device 120 to the treatment location, a guidewire lumen 508 is implemented with the distal end 510 terminated on the distal end 202 of the catheter probe 201 or catheter body 203. The proximal end 509 of the guidewire lumen 508 maybe terminated proximally along the catheter probe 201 or catheter body 203. The device 120 longitudinal configurations may include a flexible structure, rigid structure or combination of both, and maybe made of polymer, metal, metal alloys including Nitinol and combination of all.

Figure 6:
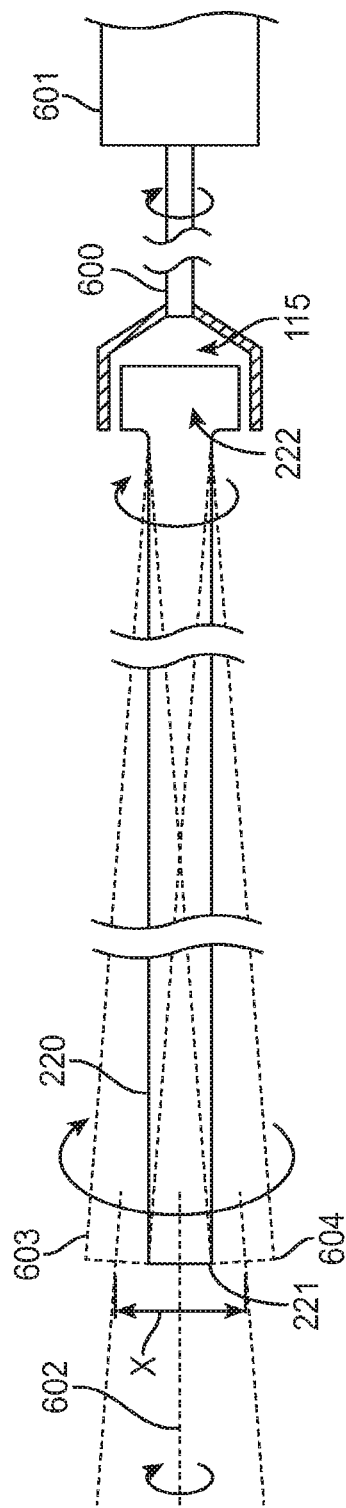
FIG. 6 shows a rotating member made of solid material having a continual cross sectional area.

FIG. 6 shows a close view of the rotational member 220 undergoing rotations around the axis 602 that is at its mass center. The distal end 221 of the rotational member 220 develops a kinetic energy directly related to its mass moment of inertia. As the distal end 221 of the rotational member 220 rotates, its kinetic energy converts to potential energy. The rotational member 220 represents a cantilever beam, a one side supported beam. The proximal insert 222 is configured for connection with the slot 115 located inside apertures 113 of the box 110 as shown in FIG. 1. The rotational member 220 is connected through the distal insert 222 into the slot 115. This juncture serves as one site support beam. Thus, the rotating shaft 220 uniformly distributes load (per unit length) causing a deflection on the distal end 221 (unsupported end). When the rotational member 220 is rotated by the shaft 600 of the motor 601 located inside the box 110 (FIG. 1), the distal end 221 will create transverse motions or displacement X from location 603 to location 604. Forces of the potential energy and transverse motion at the distal end 221 of the rotational member 220 may be utilized to break or liquefy obstructing material to be removed.

Figure 7:
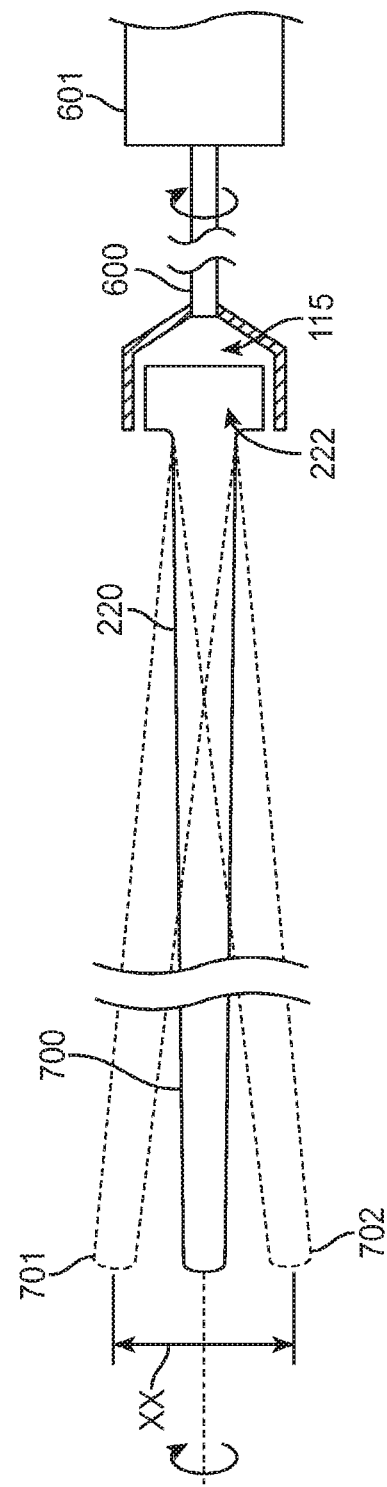
FIG. 7 shows a rotating member a distal tapered configuration.

FIG. 7 shows the rotational member 220 having a tapered distal configuration 700. Such tapering will increase deflection of the distal end 221 of the rotational member 220, and further increase its transverse motion XX from point 701 to point 702. Transverse motion frequency parameters will also increase with increase of the taper ratio.

FIGS. 8 A-D show several configuration of rotational member 220 including but not limited to continuous tapered configuration as shown in FIG. 8A. The rotational member 220 has a long continuous tapered that include all the length of the rotational member 220 which is tapered from the proximal end B to the distal end A. In another embodiment shown in FIG. 8B, the rotational member 220 comprises a continuous configuration proximally between locations C and B, and tapered configuration distally between locations B and A. FIG. 8C shows the rotational member 220 with multiple continuous configurations and multiple tapered configurations. The rotational member 220 has the first proximal segment with a continuous configuration between locations E and D, than the second proximal segment with a tapered configuration between locations D and C; following with a third segment with a continuous configuration between location C and B. The last distal segment/end of the rotational member 220 has a tapered configuration between locations B and A. FIG. 8D shows another configuration of the rotational member 220 combining a continuous configuration on the proximal end between locations D and C, with a tapered configuration between locations C and B and terminated with a reversed tapered configuration, from smaller cross section at point B to a larger cross section at point A continuously increasing between location B and A. The very distal end 221 of the rotational member 220 maybe have a variety of shapes including but not limited to sharp, rounded, fused ball, attached tip or combinations of all.

FIG. 9 shows another aspect of the present invention that includes the rotational member 220 having a primary bend or deformation 900 implemented on the distal portion of the rotational member 220. Such bend or deformation 900 will cause that the distal portion of the rotational member will undergo angular rotation around the radius 901 in addition to transverse motions (not shown). The distal portion of the rotational member 220 will undertake angular motion along the length Y from the bend 900 to distal end 221 of the rotational member 220. In practical use, forces will be applied to the obstructing material by the distal end 221 of the rotational member 220, as well as, the bend 900 which undergoes angular movement itself will further break, agitate, smash or liquefy material to be removed. Several bends maybe incorporated along the distal portion of the rotational member 220 to further increase device efficacy (not shown).

FIGS. 10A-B show similar configuration of the rotational member 220 as in FIG. 9 with exception that the very distal end 221 of the rotational member 220 comprises a primary inward bend 1000. Thus, the bend 900 becomes a secondary bend. FIG. 10B comprises a primary outward bend 1020 that is located on the distal end 221 of the rotational member 220, while having the same secondary bend 900. Such inside bend 1000 and outside bend 1020 in addition to the secondary bend 900 will add efficacy to break, liquefy and remove obstructive material. Several additional bends maybe incorporated along the distal portion of the rotational member 220 to further increase device efficacy (not shown).

Figure 11B:
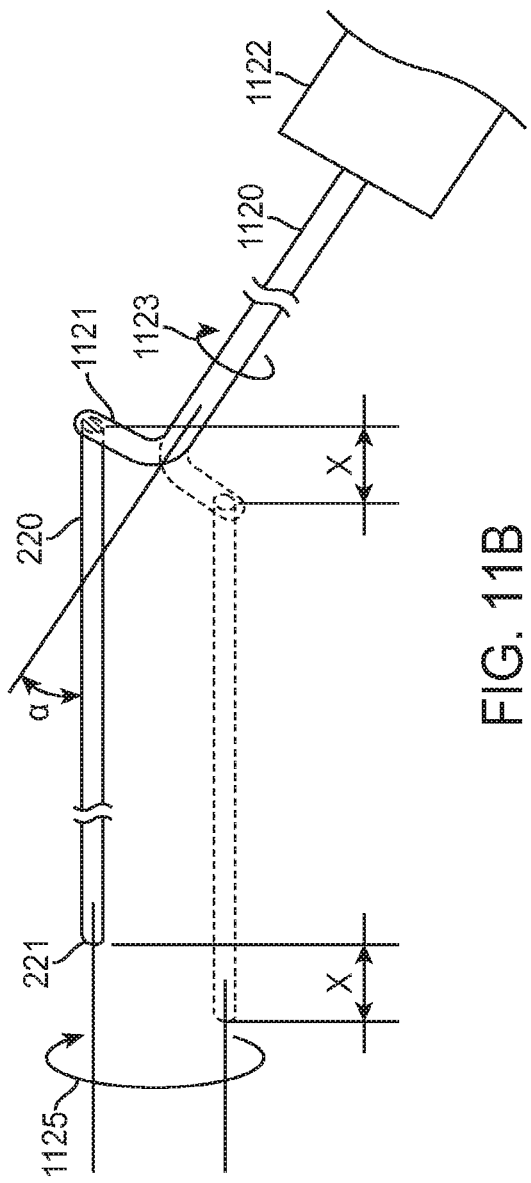

FIG. 11A-B show another embodiment of the present invention comprising the rotational member 220 reciprocal motion in addition to angular motion. FIG. 11A show an apparatus comprising the rotational member 220 connected to a cam or converter 1100 that changes rotational motion of the motor shaft 1101 shown by arrow 1102 to a reciprocal motion shown by arrow 1103 and longitudinal displacement X, The convertor 1100 also produces angular motion of the rotational member 220 as shown by arrow 1104. Such converter can be located on the rotational motor shaft 1101, on the rotational member 220 or it can be an integral part of either one. The converter 1100 consists of a flat washer or a thin circular dish 1105 that is attached to the distal end of the motor shaft 1001 at angle α. The rotational member 220 is attached off center to the circular dish 1105 at location 1106. When the motor shaft 1101 rotates along its longitudinal axis as shown by the arrow 1102, the angularly attached dish 1105 undergoes circular rotation under the angle α. In addition, off center attached rotational member 220 undergoes angular motion as show by arrow 1104. However, due to circular dish 1105 angulations at angle α, the rotational member 220 undertakes a linear back and forth motion at displacement or stroke X shown by arrow 1103. A combination of angular motion and reciprocal motion of the rotational member 220 may further increase efficacy in removing obstructive material. Embodiments including a converter to angular and reciprocal motion may have a separate motor with appropriate attachment located inside the box 110 as shown in FIG. 1 or such motor can be affixed within the structure of the device (not shown).

FIG. 11B shows anther apparatus of the present invention comprising a bend or deflection 1121 located on the distal end of the motor shaft 1120. The motor 1122 and the motor shaft 1121 are position at angle α in respect to the rotational member 220. While the shaft 1120 of the motor 1122 rotates in circular motion as shown by the arrow 1123, the distal end 221 of the rotational member 220 attached to the bend 1121 on the shaft of 1120 at the attachment point 1124 undergoes angular motion as shown by arrow 1125 and also keeps on reciprocal motion X.

In yet another embodiment of the present invention an additional element may be attached at an angle to the distal end of the rotational member 220 to produce the same effect as the bend or deflection 1121 shown in FIGS. 10A and 10B. Such element can be made of metal, metal alloy including superelastic Nitinol, polymer, ceramic, rubber or combination of all and attached to the distal end of the rotational member 220 by bonding, fusing, melting, soldering, welding and other attachment methods known in the art. Also, a similar element may be attached at the distal portion of the rotational member 220 instead of bend 900 shown in FIGS. 10A and 10B. Both such elements maybe attached to the rotational member 220 creating a similar primary bend 1000 and 1020, as well as a similar secondary bend 900 as shown in FIGS. 10A and 10B. While addition of such elements is not show on any of figures of the present invention, addition of such embodiments would be obvious for any person familiar with the art.

The method of action described and shown in FIG. 11 A-B may be used with embodiments described in FIGS. 5-10 as desired. The rotational member 220 may reciprocate at frequencies anywhere between 1 Hz-20000 Hz and stroke range can be between 0.1 mm-10 mm. Such reciprocating apparatus as show in FIG. 11A-B may comprise means for adjusting the force with which the rotational member 220 is accelerated. To this end the rotational member 220 may be spring loaded and the spring force may be varied.

Figure 12A:
FIG. 12A-D show several configurations and structures of the rotational member.
Figure 12B:
Figure 12C:
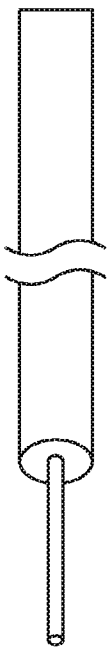
Figure 12D:

FIGS. 12A-D show several configurations of the rotational member 220. FIG. 12A shows the rotational member 220 comprising a continual solid configuration, FIG. 12B shows the rotational member 220 made of a tubular configuration; both with the same dimensions and same cross sectional area along its length. The tubular rotational member shown in FIG. 12B could be configured to deliver the irrigation fluid, thereby eliminating the need for a separate irrigation catheter 502 as shown in FIG. 5. The tubular rotational member shown in FIG. 12B could also be configured to have a closed distal end and openings at other distal locations to control where the irrigation fluid would exit from the tubular distal member (not shown). The tubular rotational member in FIG. 12 B could be made out our superelastic materials such as Nitinol. FIG. 12C shows a dual configuration of the rotational member 220 that is a combination of a continual solid member and continual tube connected together. FIG. 12D shows an example of a bundle that consists of three solid components connected to a tube component.

Rotational member 220 embodiments described and showed in FIGS. 12A-D may be made of but not limited to metal, metal alloy including Nitinol, ceramics, polymer or combination of all and have configurations comprising of but not limited to solid, hollow, multi-member or combination of all. Furthermore, rotational member 220 may have cross sectional configurations made of but not limited to circular, oval, square, rectangular or any combination of all.

FIGS. 13A-C show several embodiments of the present invention including the device for obstructive material removal having a cross sectional area decreased on the distal end. The velocity of the fluid increases as the cross sectional area decreases. According to the fluid dynamics, velocity of the fluid increases as it passes through a constriction causing increase in kinetic energy. When obstruction material to be removed through the distal end of the devices shown in FIGS. 13A-C reaches the distal narrowed end, the reduction in the cross sectional area will cause a higher pressure at the inlet. This pressure increase causes the fluid to accelerate and maintain a higher speed. This jet effect is known as Venturi effect. Very often to avoid undue drag, a tube typically has an entry cone of 30 degrees and an exit cone of 5 degrees. FIG. 13A shows the device 120 as in FIG. 5 with exception that the distal portion 1300 and the very distal end 202 of the probe 201 has a smaller cross sectional area. Such reduction of the cross sectional area may be more effective in removing material such as thrombus, clots or other liquid compositions. FIG. 13B shows another option of reducing the distal cross sectional area of the probe 201 by applying a tapered configuration 1320 distally. FIG. 13C shows a similar device as in FIG. 13B with tapered proximal configuration 1340 (larger cross sectional area of the taper) followed by a distal taper 1341 (smaller cross sectional area of the taper). In addition, a bend or deflection 1342 is implemented on the very distal end of the probe 201 or the catheter 203. This bend could be fixed or can be created by pull wires or other active means (not shown) to deflect the distal tip. The distal end 1343 of the bend 1342 is shown in upper position, and when rotated 180 degrees the very distal end of the bend 1342 moves to another position 1344. When the probe 201 is rotated around 360 degrees its distal end will be angularly directed toward obstruction material, thus significantly increasing coverage of the treatment area compare to a straight configuration shown in FIG. 13B. Distal bends maybe incorporated on the probe 201 or catheter body 203 in any device configuration described above and shown in figures as a permanent bend or elastic, flexible bend or pre-shaped bend that can form any desirable bend configuration upon one of the following but not limited to mechanical deflection, thermal activation, electrical activation or any combination of all. The bend 1342 shown in the FIG. 13C includes a very short bend 1342 on distal end of the probe 201 or the catheter 203; however, such bend maybe extended proximally and have longer length (not shown).

Although the invention has been described above with respect to certain embodiments, it will be appreciated that various changes, modifications, deletions and alterations may be made to above-described embodiments without departing from the spirit and scope of the invention. Accordingly, it is intended that all such changes, modifications, additions and deletions will be incorporated into the scope of the following claims. More specifically, description and examples have been provided that relate to treatment and removal of obstructive material from areas appropriate for treating such sites. However, the scope of the invention includes other application related to obstructive material removal from treatment sites including endovascular location, outside of endovascular locations, as well as, cancerous tissue removal, tumor or other particular target site.

Various alternative embodiments may involve use of such rotational medical devices to remove blood clots or other tissue located in other parts of a patient's body, either inside or outside of the patient's endovascular system. Locations inside the endovascular system may include, but are not limited to, the arterial system, the venous system, fistulas, vascular grafts and/or combinations thereof. Locations outside the endovascular system may include, but are not limited to, internal organs and the head. In some embodiments, one or more minor device modifications may be made to the embodiment of the system described above, to accommodate a different anatomical usage within the body. For example, in one embodiment, the blood clot removal device may have a flexible, rather than a stiff, distal portion to facilitate accessing clots in a different part of the body.

Elements or components shown with any embodiment herein are exemplary for the specific embodiment and may be used on or in combination with other embodiments disclosed herein. The invention is susceptible to various modifications and alternative forms and should not be limited to the particular forms or methods disclosed. To the contrary, the invention is to cover all modifications, equivalents and alternatives thereof.

Some scientific and theoretical considerations have been provided as to the mechanism by which the devices and therapeutic methods are effective; these considerations have been provided only for the purpose of conveying an understanding of the invention, and have no relevance to or bearing on claims made to this invention.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A device for removing obstructive material from a patient, the device comprising:
   an elongate rotational member having a distal end, a proximal end and a longitudinal axis wherein the distal end is radially offset from the longitudinal axis;
   an internal irrigation catheter at least partially surrounding the rotational member;
   an aspiration catheter at least partially surrounding the rotational member and the irrigation catheter; and
   a motor having a motor shaft that is coupled to the proximal end of the elongate rotational member, wherein the motor shaft is configured to rotate the proximal end of the elongate rotational member in an orbital manner about a longitudinal axis defined by a center of rotation of the motor shaft and to simultaneously reciprocate the elongate rotational member axially in a direction parallel to the longitudinal axis,
   wherein a distal portion of the rotational member is configured to change compliance of the obstructive material and facilitate obstructive material aspiration outside the patient.

2. The device of claim 1, wherein the rotational member comprises a length, wherein the rotational member has a shape comprising various diameters along the length.

3. The device of claim 1, wherein the rotational member has a shape selected from the group consisting of circular, oval, square and rectangular.

4. The device of claim 1, wherein the rotational member comprises a material selected from the group consisting of metals, polymers, metal alloys and combinations thereof.

5. The device of claim 1, further comprising a handle disposed on the aspiration catheter, wherein the aspiration catheter comprises an aspiration lumen, wherein the handle comprises including an aperture in fluid communication with the lumen and configured to be covered with a finger of a user to regulate application of the vacuum.

6. The device of claim 1, further comprising a radiopaque marker positioned on at least one of a distal end of the aspiration catheter or the distal end of the rotational member.

7. The device of claim 1, further comprising a guidewire lumen.

8. The device of claim 1, wherein the distal end of the rotational member has a shape selected from the group consisting of a ball shape, a flat circular end, a bent distal end, a coiled distal end, a flat deformation, a basket, and a sinusoidal shape.

9. The device of claim 1, wherein the distal portion of the rotational member includes at least one bend.

10. The device of claim 1, wherein the distal end of the rotational member is housed in a location selected from the group consisting of an inside portion of the device, an outside portion of the device, and moveable between the inside portion and the outside portion of the device.

11. A device for removing obstructive material from a human body, the device comprising:
   a rotational member having a proximal portion and a distal portion, wherein the rotational member includes at least two or more bends;
   a motor coupled to the proximal portion of the rotational member via a motor shaft, wherein the motor is configured to rotate the motor shaft in an orbital manner so that the proximal portion of the rotational member orbits about a longitudinal axis defined by a center of rotation of the motor shaft and so that the rotational member simultaneously reciprocates axially and parallel to a longitudinal axis of the rotational member;
   an aspiration catheter disposed over the rotational member; and
   means to deliver irrigation inside the aspiration catheter.

12. The device of claim 11, wherein the distal portion of the rotational member further includes at least one of the two or more bends.

13. The device of claim 11, wherein the proximal portion of the rotational member is configured to rotate axially.

14. A device for removing obstructing matter from a human body, the device comprising:
   an elongate rotational member comprising a proximal end, a distal end and a longitudinal axis;
   an aspiration catheter;
   a motor coupled to the proximal end of the elongate rotational member via a motor shaft, wherein the motor shaft is coupled to the elongate rotational member via a converter that creates a non-zero angle between the elongate rotational member and a longitudinal axis defined by a center of rotation of the motor shaft, wherein the converter is configured to simultaneously rotate so that the proximal end of the elongate rotational member orbits about the longitudinal axis of the motor shaft and so that the elongate rotational member simultaneously reciprocates axially along the longitudinal axis of the elongate rotational member; and
   an irrigation catheter.

15. The device of claim 14, wherein the elongate rotational member further comprises a distal end and a bend on the distal end.

16. The device of claim 14 wherein the distal end of the elongate rotational member is radially offset from the longitudinal axis of the elongate rotational member.

17. The device of claim 16 wherein the motor shaft is positioned at a non-zero angle relative to the elongate rotational member.

18. The device of claim 14 wherein the proximal end of the elongate rotational member is attached at a location that is off center in a radial direction with respect to a center of the converter.

19. The device of claim 18 wherein the converter comprises a flat washer.

20. The device of claim 18 wherein the converter comprises a circular dish.

21. The device of claim 14 wherein a distal portion of the device has a smaller cross sectional dimension than an adjacent proximal portion part of the device.

* * * * *